(12) United States Patent
Dinsmore

(10) Patent No.: US 6,320,932 B2
(45) Date of Patent: Nov. 20, 2001

(54) MINIATURE RADIATION SOURCE WITH FLEXIBLE PROBE AND LASER DRIVEN THERMIONIC EMITTER

(75) Inventor: Mark Dinsmore, Sudbury, MA (US)

(73) Assignee: Photoelectron Corporation, Lexington, MA (US)

( * ) Notice: Subject to any disclaimer, the term of this patent is extended or adjusted under 35 U.S.C. 154(b) by 0 days.

(21) Appl. No.: 09/748,590

(22) Filed: Dec. 22, 2000

Related U.S. Application Data

(62) Division of application No. 09/311,792, filed on May 13, 1999, now Pat. No. 6,195,411.

(51) Int. Cl.[7] .................................................. A61N 5/10
(52) U.S. Cl. ................................................ 378/65; 378/136
(58) Field of Search .............................. 378/65, 119, 136

(56) References Cited

U.S. PATENT DOCUMENTS

| | | | |
|---|---|---|---|
| 1,981,583 | 11/1934 | Craig | 99/11 |
| 2,748,293 | 5/1956 | Reinger | 240/105 |
| 3,714,486 | 1/1973 | McCrary | 313/55 |
| 3,752,990 | 8/1973 | Fischer | 250/503 |
| 3,920,999 | 11/1975 | Drexler et al. | 250/439 |
| 4,104,531 | 8/1978 | Weiss | 250/490 |
| 4,104,532 | 8/1978 | Weiss | 250/490 |
| 4,109,154 | 8/1978 | Taumann | 250/503 |
| 4,117,334 | 9/1978 | Strauts | 250/402 |
| 4,157,475 | 6/1979 | Stock et al. | 250/503 |
| 4,205,251 | 5/1980 | Zwep | 313/330 |
| 4,344,181 | 8/1982 | Baecklund | 378/45 |
| 4,517,472 | 5/1985 | Ruitberg et al. | 307/82 |
| 4,563,769 | 1/1986 | Madsen | 378/121 |
| 4,606,061 | 8/1986 | Ramamurti | 378/10 |
| 4,608,997 | 9/1986 | Brown | 128/303 B |
| 4,646,338 | 2/1987 | Skillicorn | 378/110 |
| 4,662,368 | 5/1987 | Hussein et al. | 128/303.1 |
| 4,692,938 | 9/1987 | Oba | 378/62 |
| 4,694,480 | 9/1987 | Skillicorn | 378/119 |
| 4,714,825 | 12/1987 | Oba | 250/213 |
| 4,773,413 | 9/1988 | Hussein et al. | 128/303 |
| 4,789,997 | 12/1988 | Madsen et al. | 378/109 |
| 4,821,305 | 4/1989 | Anderson | 378/136 |
| 4,852,567 | 8/1989 | Sinofsky | 128/303.1 |
| 4,856,036 | 8/1989 | Malcolm et al. | 378/116 |
| 4,921,327 | 5/1990 | Zito | 350/96.32 |
| 4,924,485 | 5/1990 | Hoeberling | 378/102 |

(List continued on next page.)

FOREIGN PATENT DOCUMENTS

| | | |
|---|---|---|
| 3543591-A | 6/1986 | (DE) . |
| 3-251263 A | 11/1991 | (JP) . |
| WO92/17243 | 10/1992 | (WO) . |

Primary Examiner—Craig E. Church
(74) Attorney, Agent, or Firm—McDermott, Will & Emery

(57) ABSTRACT

This invention is directed to a radiation source comprising a power supply, a flexible fiber optic cable assembly, a light source, and a target assembly. The power supply includes a first terminal and a second terminal, and elements for establishing an output voltage between the first terminal and the second terminal. The flexible fiber optical cable assembly has an originating end and a terminating end, and includes a fiber optical element extending from the originating end to the terminating end. The cable is adapted for transmitting light incident on the originating end to the terminating end. The light source includes elements for generating a beam of light at and directed to the originating end of the fiber optical cable assembly. The target assembly is affixed to the terminating end of the fiber optical cable assembly and is electrically coupled to the power supply by way of the first terminal and the second terminal. The target assembly includes elements for emitting radiation in a predetermined spectral range, in response to light transmitted to the terminating end.

8 Claims, 5 Drawing Sheets

U.S. PATENT DOCUMENTS

| | | | |
|---|---|---|---|
| 5,042,058 | 8/1991 | Rentzepis | 378/122 |
| 5,090,043 | 2/1992 | Parker et al. | 378/121 |
| 5,116,344 | 5/1992 | Sundqvist | 606/130 |
| 5,116,345 | 5/1992 | Jewell et al. | 606/130 |
| 5,147,353 | 9/1992 | Everett | 606/15 |
| 5,153,900 | 10/1992 | Nomikos et al. | 378/65 |
| 5,165,093 | 11/1992 | Miller et al. | 378/138 |
| 5,428,658 * | 6/1995 | Oettinger et al. | 378/136 |
| 5,576,549 | 11/1996 | Hell et al. | 250/423 |
| 5,729,583 | 3/1998 | Tang et al. | 378/122 |

* cited by examiner

MINIATURE RADIATION SOURCE WITH FLEXIBLE PROBE AND LASER DRIVEN THERMIONIC EMITTER

RELATED APPLICATIONS

The following application is a divisional application of U.S. patent application Ser. No. 09/311,792, filed May 13, 1999 now U.S. Pat. No. 6,195,411.

BACKGROUND OF THE INVENTION

The present invention relates to a highly miniaturized, low power, programmable radiation source for use in delivering predefined doses of radiation to a predefined region and more particularly to a miniaturized radiation source mounted in a flexible probe.

In the field of medicine, radiation is used for diagnostic, therapeutic and palliative treatment of patients. The conventional medical radiation sources used for these treatments include large fixed position machines as well as small, transportable radiation generating probes. The current state of the art treatment systems utilize computers to generate complex treatment plans.

These systems apply doses of radiation that are known to inhibit the growth of new tissue because the radiation affects dividing cells more than the mature cells found in nongrowing tissue. Thus, the tissue in the site of an excised tumor can be treated to prevent the regrowth of cancerous tissue and the recurrence of cancer. Alternatively, radiation can be applied to other areas of the body to inhibit tissue growth, for example the growth of new blood vessels inside the eye that can cause macular degeneration.

Conventional radiation treatments systems, such as the LINAC used for medical treatment, utilize a high power remote radiation source and direct a beam of radiation at a target area, such as tumor inside the body of a patient. This type of treatment is referred to as teletherapy because the radiation source is located a predefined distance, approximately one meter, from the target. This treatment suffers from the disadvantage that tissue disposed between the radiation source and the target is exposed to radiation.

An alternative treatment system utilizing a point source of radiation is disclosed in U.S. Pat. No. 5,153,900 issued to Nomikos et al., U.S. Pat. No. 5,369,679 to Sliski et al., and U.S. Pat. No. 5,422,926 to Smith et al., all owned by the assignee of the present application, all of which are hereby incorporated by reference. This system includes a miniaturized, insertable probe capable of producing low power radiation in predefined dose geometries disposed about a predetermined location. This type of treatment is referred to as brachytherapy because the source is located close to or in some cases within the area receiving treatment. One advantage of brachytherapy is that the radiation is applied primarily to treat a predefined tissue volume, without significantly affecting the tissue adjacent to the treated volume.

Typical radiation therapy treatment involves positioning the insertable probe into or adjacent to the tumor or the site where the tumor or a portion of the tumor was removed to treat the tissue adjacent the site with a "local boost" of radiation. In order to facilitate controlled treatment of the site, it is desirable to support the tissue portions to be treated at a predefined distances from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

In many x-ray therapeutic procedures, x-ray probes of the type generally disclosed in U.S. Pat. No. 5,153,900 incorporate a relatively rigid tube enclosing an electron beam directed to an x-ray emitting target at its distal end. For example, in treatment of brain tumors, an x-ray probe having a rigid tube is used with a stereotactic frame affixed to the patient's skull, where the tube is advanced into a biopsy hole to the tumor location, as disclosed in U.S. Pat. No. 5,369,679. The rigidity of the tube is useful in ensuring that the x-ray emitting target is properly located. In other cases, it is desirable to have a flexible tube leading to the x-ray emitting target, for example, where it is desirable to pass the probe up the urethra to the bladder, for treatment of the bladder. Such a flexible probe is disclosed in U.S. Pat. No. 5,248,658.

However, it has been difficult to effectively treat tissue using the flexible probe of the latter patent.

Accordingly, it is an object of the present invention to provide an improved system for delivering radiation to a localized area.

It is a further object of the present invention to provide an improved highly miniaturized radiation source with a flexible probe.

SUMMARY OF THE INVENTION

The present invention is directed to a miniaturized radiation source at the end of a flexible probe or catheter. The flexible catheter extends along a probe axis between a proximal end and a distal end of the catheter. The radiation source, at the distal end of the catheter, includes a substantially rigid housing disposed about a substantially evacuated interior region extending along a beam axis from an electron source at an input end of the housing to a radiation transmissive window at an output end of the housing. The housing also includes a channel electron multiplier adapted for receiving electrons from the electron source and for producing free electrons at an output end of the channel electron multiplier and an electron accelerator adapted for establishing a potential difference in the interior region of the housing whereby the free electrons produced at the output end of the channel electron multiplier are accelerated toward a target at or near the window. The target produces x-radiation in response to incident accelerated free electrons.

Preferably, the electron accelerator includes a surface disposed about the beam axis between the electron source and the target on a ceramic and preferably monolithic, substrate. In one embodiment, the surface bears a semiconductor coating. The surface may be substantially conical in shape wherein the distance from the beam axis increases as a function of the distance from the electron source. The electron source can be a photocathode illuminated by laser energy, a field emitter or a thermionic emitter. The target and outer surface of the probe is preferably maintained at ground potential to reduce the risk of shock.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

The present invention is directed to a miniature, low power radiation producing probe which can be used for diagnostic, therapeutic and palliative treatment of patients. The radiation source in accordance with the present invention can made smaller than conventional radiation sources. In addition, the radiation source can be disposed at the distal end of the tip of a flexible (or rigid) tube or catheter which can be inserted into the body. In one embodiment, only a single high voltage wire is necessary for operation. The target and the outer surface of the probe are set at the ground potential to reduce the shock hazard of the device.

Figure 1A:
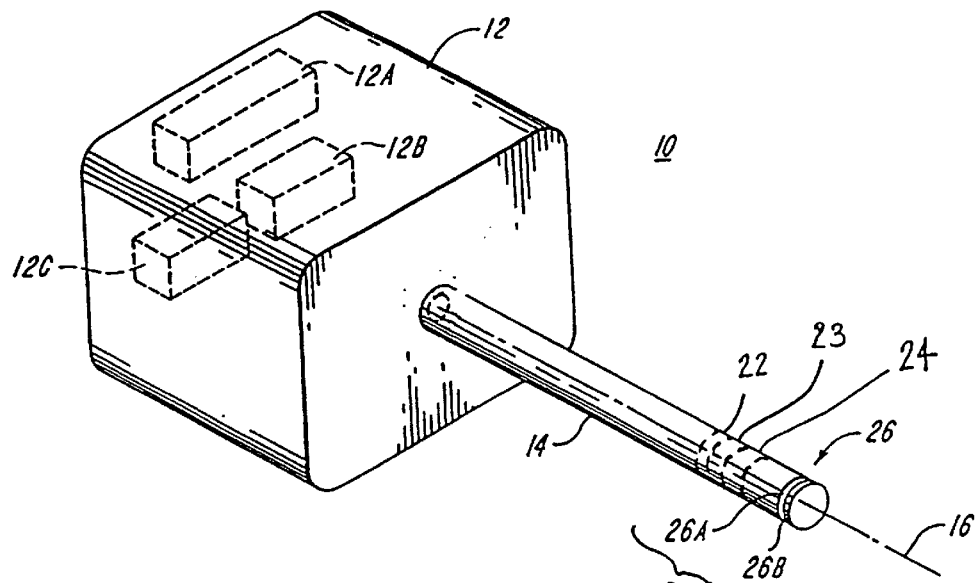
FIGS. 1A and 1B are a diagrammatic perspective view and a diagrammatic detail view, respectively, of a low power radiation source embodying the present invention.

FIG. 1A shows an x-ray apparatus 10 embodying the present invention. Apparatus 10 includes a housing 12 and an elongated cylindrical probe 14 extending from housing 12 along a reference axis 16 to an x source assembly 19. Preferably, the probe 14 is flexible, as described below, but in some cases may be rigid. The housing 12 encloses a high voltage power supply 12A, a battery 12B and a control system 12C. The x-ray source assembly 19 has an electron source (cathode) 22 located in the distal end of the probe 14. Electron source 22 is located in close proximity to a channel electron multiplier (CEM) 23 which receives electrons from the electron source 22. An accelerator 24 is positioned between the CEM 23 and an x-ray emitting (in response to incident accelerated electrons) target 26. The target underlies on x-ray transmissive window 27. Probe 14 is integral with the housing 12 and extends toward the target 26. In various embodiments, the x-ray emitting tip may be selectively shielded to control the spatial distribution of x-rays. In addition, the accelerator 24 may be magnetically shielded to prevent external magnetic fields from deflecting the beam away from designed impact points on the target.

Figure 1B:
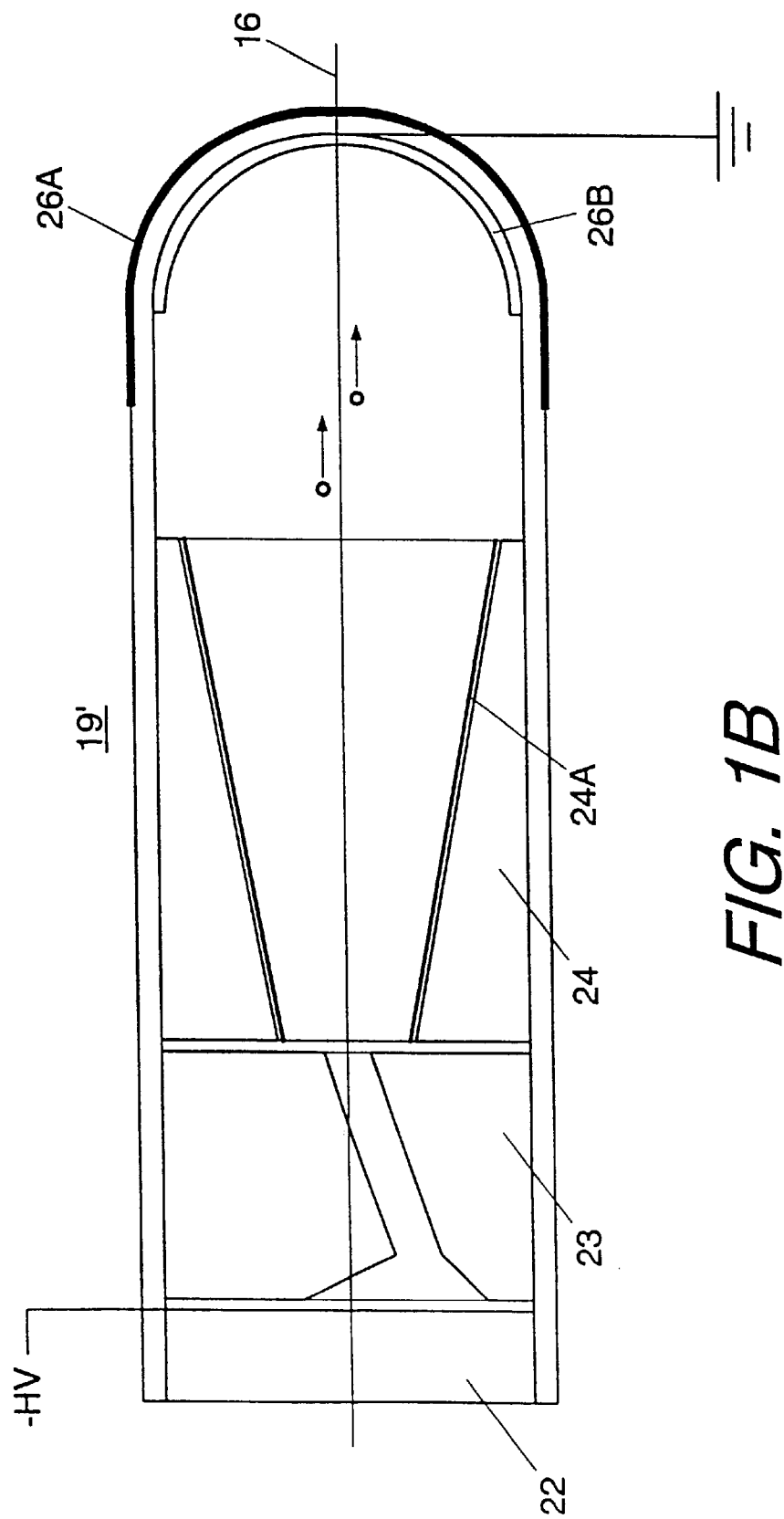

FIG. 1B shows an x-ray source assembly 19' for generating x-rays embodying the present invention. That source 19' is adapted for placement at the end of a cylindrical element (flexible or rigid). In an alternate form, shown in FIG. 2A and 2B, an x-ray source 19" is positioned within a compact housing 12, the latter device is suitable to applying x-radiation body surface tissue.

In the various forms of x-ray source assembly 19, the electron beam generator 22 may include a thermionic emitter (driven by a low voltage power source or laser) or a photocathode (irradiated by an LED or laser source) or a field emitter. A single high voltage power supply 12A can be used to power the electron source (thermionic emitter) 22, the CEM 23 and accelerator 24. The accelerator 24 establishes an acceleration potential difference between the CEM 23 and the target 26 which is at ground potential. The beam generation and acceleration components can be adapted to establish a thin (e.g. 1 mm or less in diameter) electron beam within the assembly 19 along a nominally straight axis 16.

Preferably, the CEM 23 is constructed as is well known and the electron multiplication value is predetermined as function of the intended use of the radiation source. Preferably, a high voltage of 1 Kvol is connected to input end of the CEM.

Preferably, the accelerator is constructed from a monolithic ceramic material and includes an interior channel formed in the shape of the surface of a cone, although other shapes may be used, for example parabolic. The accelerator is disposed between the CEM 23 and the target 26 along the axis of the electron beam trajectory whereby the distance of the surface from the beam increases as a function of the distance from the CEM23. Preferably, the surface includes a semiconductive coating 24A which ensures that the voltage gradient in the accelerator is smooth and linear and helps to prevent breakdown which occurs when the electrons hit the walls of the accelerator.

In one form of the invention, the outer cylindrical portion of the x-ray source assembly 19 is a hollow evacuated cylinder made of a molybdenum-rhenium, (Mo—Re), molybdenum (Mo) or mu-metal body with an interior diameter of 2 mm, and an exterior diameter of 3 mm. Preferably, beryllium (Be) cap and having a distance from the electron source to the target is less than 2 mm. The target assembly 26 includes an emission element consisting of a small beryllium (Be) target element 26A which is coated on the side exposed to the incident electron beam with a thin film or layer 26B of a high-Z element, such as tungsten (W), uranium (U) or gold (Au). By way of example, with electrons accelerated to 30 keV-, a 2.2 micron thick tungsten film absorbs substantially all the incident electrons, while transmitting approximately 95% of any 30 keV-, 88% of any 20 keV-, and 83% of any 10 keV- x-rays generated in that layer. In the preferred embodiment, the beryllium target element 26A is 0.5 mm thick with the result that 95% of the x-rays generated in directions normal to and toward the substrate 26A, and having passed through the tungsten target, are then transmitted through the beryllium substrate and outward at the distal end of assembly 19. While the target element 26A shown in FIG. 3B is in the form of a hemispherical layer, other shaped elements may be used, such as those having disk-like or conical shapes.

In some forms of the target, the window element 26A may include a multiple layer film 26B, where the differing layers may have different emission characteristics. By way of example, the first layer may have an emission (vs. energy) peak at a relatively low energy, and the second (underlying) layer may have an emission (vs. energy) peak at a relatively high energy. With this form of the invention, a low energy electron beam may be used to generate x-rays in the first layer (to achieve a first radiation characteristic) and high energy electrons may be used to penetrate through to the underlying layer (to achieve a second radiation characteristic). As an example, a 0.5 mm wide electron beam is emitted at the cathode and accelerated to 30 keV- through the anode, with 0.1 eV transverse electron energies, and arrives at the target assembly 26 downstream from the anode, with a beam diameter of less than 1 mm at the target assembly 26. X-rays are generated in the target assembly 26 in accordance with preselected beam voltage, current, and target element 26B composition. The x-rays thus generated pass through the beryllium target substrate 26A with minimized loss in energy. As an alternative to beryllium, the target substrate 26A may be made of carbon or other suitable material which permits x-rays to pass with a minimum loss of energy. An optimal material for target substrate 26A is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

Figure 2A:
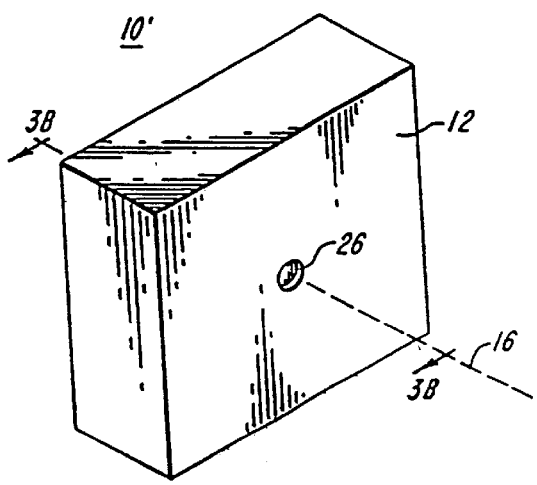
FIGS. 2A and 2B are a perspective view and a sectional view, respectively, of an alternate form embodying the present invention.
Figure 2B:
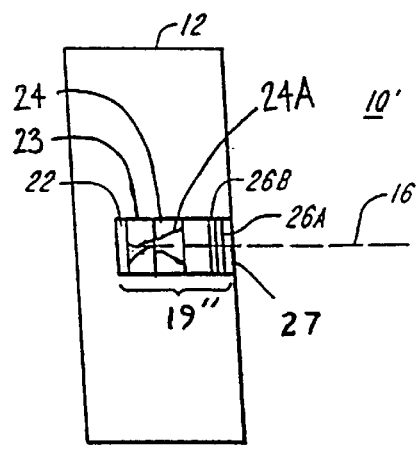

The apparatus of FIGS. 2A and 2B is particularly adapted for full implantation into a patient, where the housing 12 a biocompatible outer surface and encloses both a high voltage power supply circuit 12A for establishing a drive voltage for the beam generator 22, and an associated battery 12B for driving that circuit 12A. In this case, an associated controller 12C establishes control of the output voltage of the high power supply circuit 12A, in the manner described below.

The apparatus of FIGS. 1A and 1B may be used in a manner where only the probe 14 and x-ray source assembly 19 are inserted into a patient while the housing 12 remains outside the patient, i.e., a transcutaneous form. In the latter form, some or all of the various elements shown within housing 12 may alternatively be remotely located.

Figure 3:
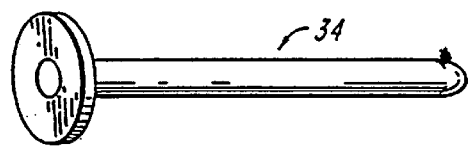
FIG. 3 is a diagrammatic representation of a sheath adapted for use with the apparatus of FIG. 1.

In the transcutaneous form, the apparatus 10 may be used with an elongated closed end (or cup-shaped) sheath 34, as shown in FIG. 3, having a biocompatible outer surface, for example, fabricated of medical grade aliphatic polyurethane, as manufactured under the trademark Tecoflex by Thermedics, Inc., Woburn, Mass. With this configuration, the probe 14 is first inserted into the sheath 34. The sheath 34 and probe 14 are then inserted into the patient through the skin. Alternatively, a port may be inserted through the skin and attached to it, as for example a Dermaport port manufactured by Thermedics Inc., Woburn, Mass. The probe 14 is then inserted into the port.

The lining of the sheath or port can be configured as an x-ray shield by introducing barium sulfate or bismuth trioxide, or other x-ray shielding materials, into the sheath. If necessary, the probe 14 and housing 12 can be secured to the patient's body to prevent any relative motion during the extended time of treatment. An exemplary sheath 34 is shown in FIG. 3.

In one embodiment of the apparatus as shown in FIGS. 1A and 1B, the main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium or alloys of these materials. The outer cylindrical shell of the accelerator 24 can be made of the outer shell metal. The inner or outer surface of probe 14 can then be coated with a high permeability magnetic alloy such as permalloy (approximately 80% nickel and 20% iron), to provide magnetic shielding. Alternatively, a thin sleeve of mu-metal can be fitted over, or inside of that shell of accelerator 24. The x-ray apparatus 10 can then be used in environments in which there are dc and ac magnetic fields due to electrical power, the field of the earth, or other magnetized bodies nominally capable of deflecting the electron beam from the probe axis.

In implantable configurations, such as those of FIGS. 2A and 2B, the power supply 12A and target assembly 26 are preferably enclosed in a capsule to prevent current flow from the x-ray source to the patient. The closed housing 12 and probe 14 are, thus, encapsulated in a continuous outer shell of appropriate shielding material such as those mentioned previously.

The high voltage power supply 12A in each of the illustrated embodiments preferably satisfies three criteria: 1) small in size; 2) high efficiency to enable the use of battery power; and 3) independently variable x-ray tube voltage and current to enable the unit to be programmed for specific applications. A high-frequency, switch-mode power converter is used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components.

The embodiment of FIGS. 2A and 2B can also be adapted for superficial usage, that is for direct placement on the skin of a patient. This form of the invention is particularly useful for x-ray treatment of skin lesions or tumors, or other dermatological applications. In FIGS. 2A and 2B, elements that correspond to elements in the embodiment of FIGS. 1A and 1B are denoted with the same reference designations. Apparatus 10' generates an electron beam in a channel 40 enclosed within housing 12, where that channel 40 corresponds to probe 14. In the present embodiment, of FIGS. 2A and 2B, the x-ray source assembly 19 functions in a manner similar to that described above. With the configuration of FIGS. 2A and 2B, low power x-rays may be directed to a desired skin region of a patient.

In all of the above-described embodiments, the x-ray emission element of the target assembly is adapted to be adjacent to or within the region to be irradiated. The proximity of the emission element to the targeted region, e.g. the tumor, eliminates the need for the high voltages of presently used machines, to achieve satisfactory x-ray penetration through the body wall to the tumor site. The low voltage also concentrates the radiation in the targeted tumor, and limits the damage to surrounding tissue and surface skin at the point of penetration. For example, the delivery of 4000 rads, as is required after a mastectomy, with a 40 kV, 20 uA electron beam, may require approximately 1 to 3 hours of radiation. However, since the x-ray source is, in this preferred embodiment, insertable proximate to, or into, the region-to-be-irradiated risk of incidental radiation exposure to other parts of the patient's body is significantly reduced.

Further, specificity in treating tumors may be achieved by tailoring the target and shield geometry and material at the emission site, for example as disclosed in U.S. Pat. No. PHLL-111, assigned to the assignee of the present invention,. This tailoring facilitates the control of energy and the spatial profile of the x-ray emission to ensure more homogenous distribution of the radiation throughout the targeted tumor.

Figure 4:
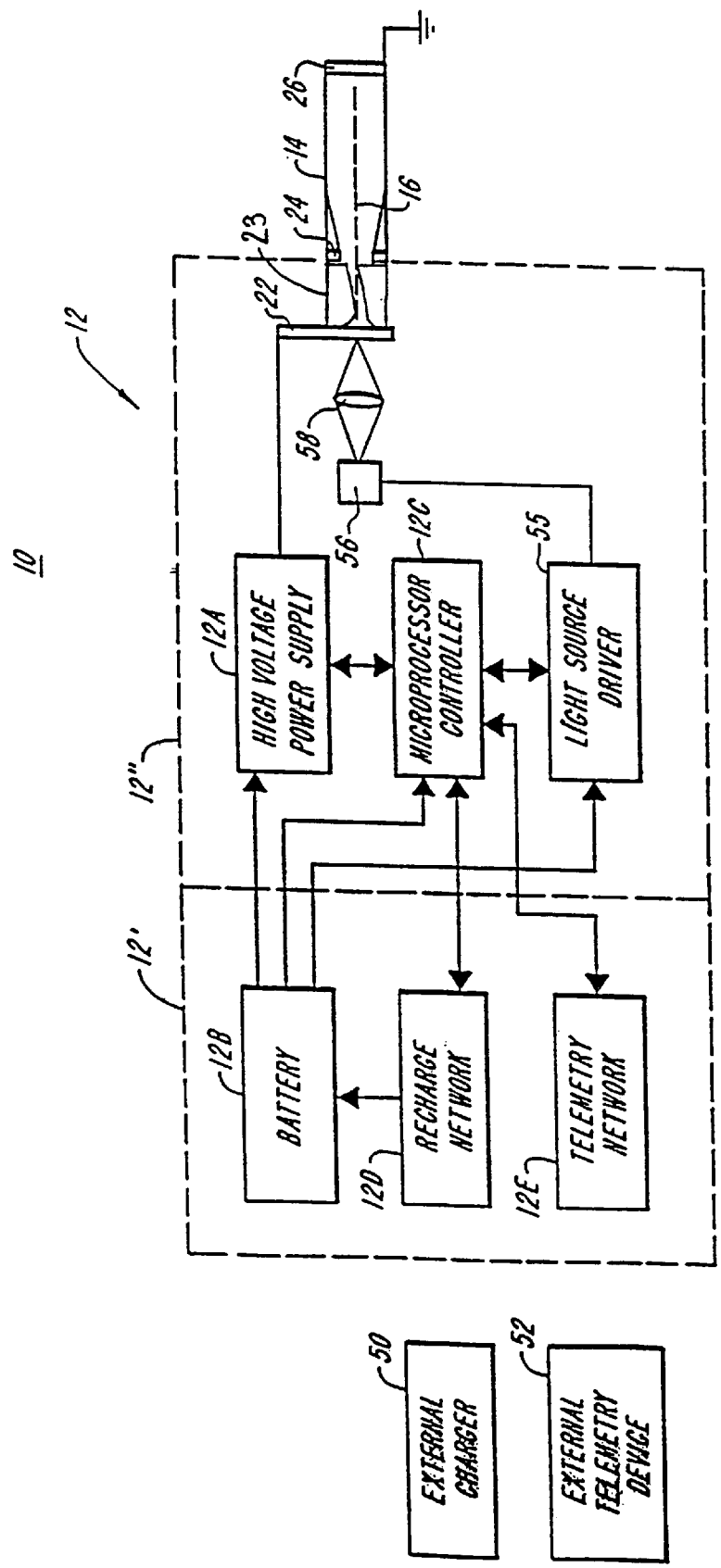
FIG. 4 is a schematic block diagram of the embodiment of FIG. 1.

FIG. 4 is a schematic representation of the x-ray source apparatus 10 shown in FIG. 1A. In that preferred configuration, the housing 12 is divided into a first portion 12' and a second portion 12". Enclosed within the first housing portion 12' is a rechargeable battery 12B, a recharge network 12D for the battery 12B, which is adapted for use with an external charger 50, and a telemetry network 12E, adapted to be responsive to an external telemetry device 52 to function in the manner described below. That portion 12' is coupled by cables to the second housing portion 12". The second housing portion 12" includes the high voltage power supply 12A, controller 12C and the probe 14, as well as the electron beam generating element 22. In one embodiment, the electron beam generator includes a thermionic emitter 22 driven by the power supply 12A. In operation, power supply 12A heats the thermionic emitter 22, which in turn generates electrons which are then accelerated toward the anode 24. The anode 24 attracts the electrons, but passes them through its central aperture toward the target assembly 26. The controller 12C controls the power supply 12A to dynamically adjust the cathode voltage, the electron beam current, and temporal parameters, or to provide pre-selected voltage, beam current, and temporal parameters.

Also illustrated, is an alternative electron beam generator which includes a photoemitter 22 irradiated by a light source 56, such as a diode laser or LED, powered by a driver 55. The light is focused on the photoemitter 22 by a focusing lens 58.

In the illustrated embodiment, external telemetry device 52 and telemetry network 12E cooperate to permit external control (dynamic or predetermined) control over the power supply 12A and temporal parameters. In embodiments when the housing 12" is not implanted, but where only probe 14 extends into a patient's body, the controller 12C may directly be used to control operation and in that case there is no need for network 12E.

Figure 5:
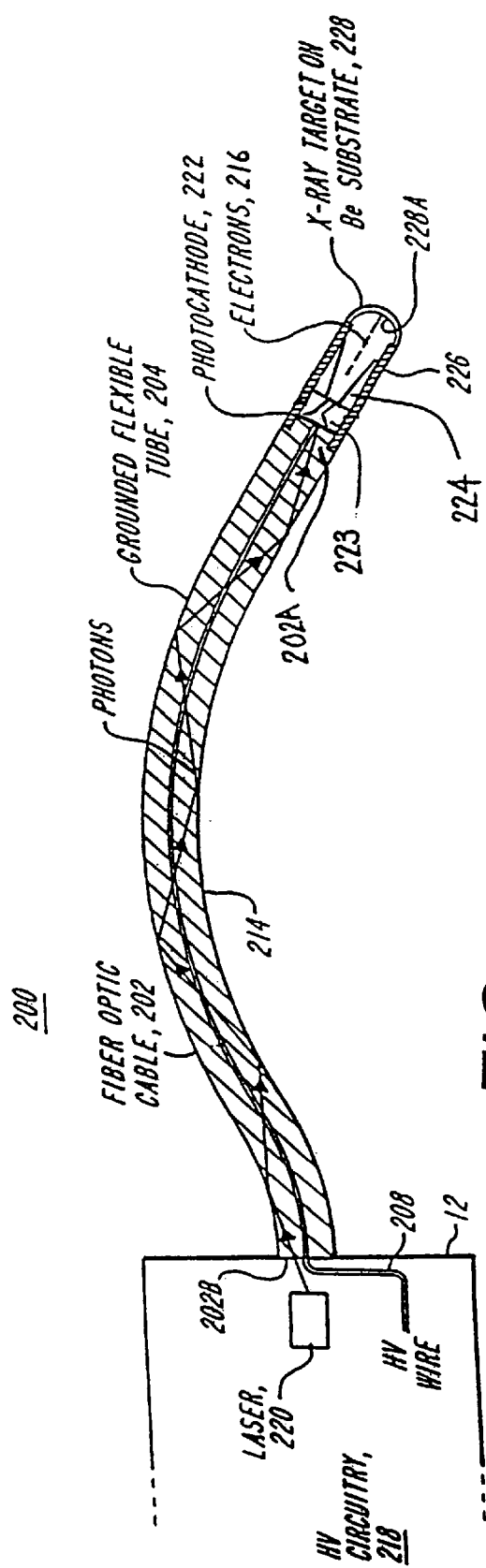
FIG. 5 is a diagrammatic view of a low power radiation treatment system having a flexible probe embodying the present invention.
Figure 6:
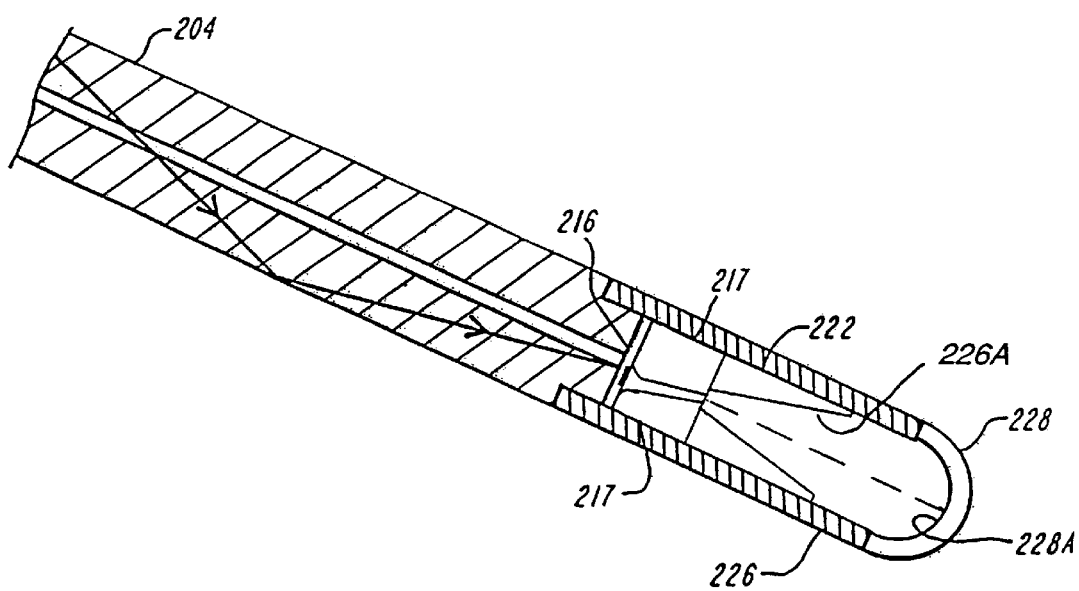
FIG. 6 is a diagrammatic view of a low power radiation source embodying the present invention.

FIGS. 5 and 6 show a diagrammatic view of radiation treatment apparatus 200 including a flexible probe 214. The apparatus 200 includes a high voltage source 218, a laser (or other optical) source 220, a probe assembly 214, and a radiation source assembly 226. According to one aspect of the invention, the apparatus 200 provides the required flexibility, without using strong magnetic fields, by locating electron source components 222, 223 and accelerator 224 near the target 228 in the distal end of the probe 214. The probe assembly 214 couples both the laser source 220 and the high voltage feed 218 to the radiation source assembly 226. Preferably, the probe assembly includes flexible fiber optical cable 202 enclosed in a small-diameter flexible metallic tube 204.

The radiation source assembly 226, which can be for example 1 to 2 cm in length, extends from the end of the probe assembly 214 and includes a shell which encloses the target 228. According to one embodiment, the radiation source assembly 226 is rigid in nature and generally cylindrical in shape. In this embodiment the cylindrical shell enclosing the radiations source assembly 226 can be considered to provide a housing for the electron beam source as well as a tubular probe extending from the housing along the electron beam path. The inner surface 226A of the assembly 226 is lined with an electrical insulator, while the external surface of the assembly 226 is electrically conductive. According to a preferred embodiment, the radiation source assembly is hermetically sealed to the end of the probe assembly 214, and evacuated. According to another embodiment, the entire probe assembly 214 is evacuated.

The terminal end 202A of the fiber optical cable 202 is preferably coated, over at least part of its area, with a semitransparent photoemissive substance such as, Ag—O—Cs, thus forming a photocathode 222. A high voltage conductor 208, embedded in the fiber optical cable 202, conducts electrons to the cathode 222 (if necessary), the electron multiplier 223 and the accelerator 224 from the high voltage source 218. Similarly, the flexible tube 204 couples a ground return from the target 228 to the high voltage source 218, thereby establishing a high voltage field between the cathode 216 and the target 228. The fiber optical cable 202 acts as an insulating dielectric between the high voltage conductor 208 and the grounded flexible tube 204.

In order to eliminate scattering of the light in the fiber optic cable 202 by the high voltage wire 208, the fiber optic cable 202 can have an annular configuration. The light from the laser 220 travels down the annular core of the fiber optic cable 202. Cladding can be provided on each side of the core having an index of refraction so as to reflect the light beam incident on the interface back into the core. The grounded flexible metal tube 204 can surround the outer cladding.

As in previously described embodiments, the target 228 can be for example, beryllium, (Be), coated on one side with a thin film or layer 228A of a higher impedance element, such as tungsten (W) or gold (Au).

In operation, the small semiconductor laser 220 shining down the fiber optical cable 202 activates the transmissive photocathode 222 which generates free electrons 216. The high voltage field between the cathode 222 and target 228 accelerates these electrons, thereby forcing them to strike the surface 228A of target 228 and produce x-rays. In order to generate, for example, 20 uA of current from an Ag—O—Cs photocathode 222 with a laser 220 emitting light at a wavelength of 0.8 m, the 0.4% quantum efficiency of this photocathode 222 for this wavelength requires that the laser 220 emits 7.5 mW optical power. Such diode lasers are readily commercially available. According to the invention, the photoemissive surface which forms cathode 222 can, in fact, be quite small. For example, for a current density at the cathode 222 of 1 A/cm$^2$, the photoemitter's diameter need only be approximately 50 $\mu$m.

One difficult fabrication aspect of this invention is the fabrication of the photocathode 222, which for practical substances, with reasonable quantum efficiencies above $10^{-3}$, should be performed in a vacuum. This procedure can be carried out with the fiber optical cable 202 positioned in a bell jar, where for example, an Ag—O—Cs photosurface is fabricated in the conventional manner. Subsequently, without exposure to air, the optical cable 202 can be inserted into the tube 204. The end 202B can be vacuum sealed to the flexible tube 204.

In the above embodiments, the probe 14 or 214, along with its associated target 26, or 228, can be coated with a biocompatible outer layer, such as titanium nitride on a sublayer of nickel. For additional biocompatibility, a sheath of, for example, polyurethane can be fitted over the probe, such as that illustrated in FIG. 3.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A therapeutic radiation source, comprising:
   A. a flexible catheter extending along a probe axis between a proximal end and a distal end of the catheter, the flexible catheter comprising optical delivery means extending along said probe axis and having an originating end and a terminating end, and adapted for transmitting optical radiation incident on said originating end to said terminating end;
   B. an optical source, including means for generating a beam of optical radiation directed to said originating end of said optical delivery means;
   C. a radiation source coupled to said terminating end of said optical delivery means, comprising a substantially rigid housing enclosing an electron source and a target, said housing defining a substantially evacuated interior region extending along a beam axis between said electron source at an input end of the housing and a radiation transmissive window at an output end of the housing, a. wherein said electron source and said target are disposed along said beam axis and spaced apart from and opposite each other;

b. wherein said electron source is adapted to emit electrons in response to optical radiation transmitted to said terminating end, and comprises a thermionic emitter having an electron emissive surface; and c. wherein said target is responsive to incident electrons to emit therapeutic radiation whereby therapeutic radiation emitted therefrom is directed through the radiation transmissive window; and D. means for establishing an accelerating electric field extending between said electron source toward said target, the electric field acting to accelerate electrons emitted from said electron source toward said target;

wherein said optical delivery means are adapted for directing a beam of optical radiation transmitted therethrough to impinge upon said surface of said thermionic emitter, and wherein said beam of transmitted optical radiation has a power level sufficient to heat at least a portion of said surface to an electron emitting temperature so as to cause thermionic emission of electrons from said surface.

2. A therapeutic radiation source according to claim 1, wherein said optical source is a laser, and wherein said beam of optical radiation is substantially monochromatic and coherent.

3. A therapeutic radiation source according to claim 1, wherein said therapeutic radiation comprises x-rays.

4. A therapeutic radiation source according to claim 1, wherein said optical delivery means comprises a fiber optical cable assembly having a fiber optical element extending from said originating end to said terminating end.

5. A therapeutic radiation source according to claim 4, wherein the means for establishing an accelerating electric field comprises:

a power supply, having a first terminal and a second terminal, and a drive means for establishing an output voltage between said first terminal and said second terminal, said power supply being electrically coupled to said radiation source by way of said first terminal and said second terminal.

6. A therapeutic radiation source according to claim 4, wherein said fiber optical cable assembly further comprises:

A. an electrically conductive cable, wherein said fiber optical element is concentrically disposed around said electrically conductive cable; and B. an electrically conductive outer shell, concentrically disposed around said fiber optical element, said fiber optical element forming an optically transmissive core.

7. A therapeutic radiation source according to claim 6, wherein said fiber optical cable assembly further comprises a first cladding shell, said first cladding shell having an index of refraction less than the index of refraction of said optically transmissive core and being concentrically disposed between said electrically conductive cable and said fiber optical element.

8. A therapeutic radiation source according to claim 7 wherein said fiber optical cable assembly further comprises a second cladding shell, said second cladding shell having an index of refraction less than the index of refraction of said optically transmissive core and being concentrically disposed between said fiber optical element and said electrically conductive outer shell.

* * * * *